(12) United States Patent
Tripp et al.

(10) Patent No.: US 8,388,645 B2
(45) Date of Patent: Mar. 5, 2013

(54) INTRAVASCULAR FILTER RESTRAINING DEVICE

(75) Inventors: Grace Tripp, Chanhassen, MN (US); Michele Zoromski, Minneapolis, MN (US); Jim Anderson, Chanhassen, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 364 days.

(21) Appl. No.: 12/643,029

(22) Filed: Dec. 21, 2009

(65) Prior Publication Data

US 2011/0152916 A1    Jun. 23, 2011

(51) Int. Cl.
*A61M 29/00*    (2006.01)
*A61F 2/06*    (2006.01)

(52) U.S. Cl. ...................................... 606/200; 623/1.11

(58) Field of Classification Search .................. 606/108, 606/191, 194, 200; 623/1.11, 1.12, 1.22, 623/23.7

See application file for complete search history.

(56) References Cited

U.S. PATENT DOCUMENTS

| | | | |
|---|---|---|---|
| 5,716,410 A * | 2/1998 | Wang et al. .................... | 606/191 |
| 6,019,787 A | 2/2000 | Richard | |
| 6,506,203 B1 | 1/2003 | Boyle | |
| 6,613,072 B2 * | 9/2003 | Lau et al. ...................... | 623/1.11 |
| 6,685,648 B2 * | 2/2004 | Flaherty et al. ............... | 600/464 |
| 6,878,153 B2 | 4/2005 | Linder | |
| 6,884,257 B1 * | 4/2005 | Cox ............................. | 623/1.11 |
| 6,997,939 B2 | 2/2006 | Linder | |
| 2002/0099436 A1 | 7/2002 | Thornton | |
| 2005/0043786 A1 * | 2/2005 | Chu et al. ...................... | 623/1.42 |
| 2005/0085848 A1 | 4/2005 | Johnson | |
| 2005/0096692 A1 | 5/2005 | Linder | |
| 2005/0154443 A1 * | 7/2005 | Linder et al. .................. | 623/1.11 |
| 2005/0283185 A1 | 12/2005 | Linder | |
| 2006/0089666 A1 | 4/2006 | Linder | |

\* cited by examiner

*Primary Examiner* — Gary Jackson
*Assistant Examiner* — Lindsey Bachman
(74) *Attorney, Agent, or Firm* — Seager, Tufte & Wickhem LLC (57) ABSTRACT

A filtering device includes a filter that captures embolic material, a plurality of biased support struts that expand outwardly to deploy the filter, and a restraining mechanism. The restraining mechanism applies a restraining force that prevents the plurality of biased support struts from expanding outwardly to deploy the filter. An actuating member cooperates with a portion of the restraining mechanism to release the restraining force and allow the filter to deploy.

7 Claims, 9 Drawing Sheets

INTRAVASCULAR FILTER RESTRAINING DEVICE

FIELD

This disclosure relates generally to implantable medical devices and more particularly relates to intravascular filter devices that are configured for percutaneous insertion into the blood vessel of a patient.

BACKGROUND

Human blood vessels may become occluded or blocked by plaque, thrombi, or other material that reduce the blood carrying capacity of the vessel. Should the blockage occur at a critical place in the circulatory system, serious injury or death may result. Medical intervention can be performed when such an occlusion is detected.

Several procedures are now used to open these occluded vessels, including angioplasty, atherectomy, and stenting. Angioplasty is a well known procedure that uses an inflatable balloon to dilate the occlusion. Atherectomy involves removing the matter occluding the vessel through one of a variety of means, and the process may sometimes be repeated until a sufficient amount of material has been removed to restore blood flow to an acceptable level. Stenting involves temporarily or permanently implanting a substantially cylindrical tube or mesh sleeve into the occluded area of a vessel to radially open the lumen of the vessel. During any of these procedures, material may be separated from the wall of the blood vessel. This separated material can enter the bloodstream, and may be large enough to occlude smaller downstream blood vessels, potentially blocking blood flow to tissue. Intravascular filters are commonly used to capture this separated material during the procedure.

However, it is possible to dislodge some of this material during the placement or introduction of the devices used in the procedure. Therefore, there exists a need to improve operation of the devices during the insertion process.

SUMMARY

This disclosure pertains generally to intravascular filter devices such as embolic protection filters and pertains more particularly to intravascular filters with improved insertion characteristics. Accordingly, an illustrative but non-limiting example may be found in a restraining mechanism for an intravascular filtering device that may include a ribbon fixedly attached to the device and adapted to wrap around the filter and apply a restraining force to a plurality of support struts of the filtering device. The device may also include an actuating member slidably engaged with a tubular member attached to the ribbon. The actuating member may be configured to release the restraining force to allow outward expansion of the plurality of support struts upon moving the actuating member in a proximal direction. The ribbon and a tubular member may have any one or more of a number of additional characteristics including material type, coating, and integration with other components.

Another illustrative but non-limiting example may be found in a restraining mechanism for an intravascular filtering device that may include a ribbon adapted to wrap around the filter and apply a restraining force to a plurality of support struts of the filtering device. The device may also include an actuating member slidably engaged with two tubular members attached to the ribbon. The actuating member may be configured to release the restraining force to allow outward expansion of the plurality of support struts upon moving the actuating member in a proximal direction. The ribbon may be non-removably coupled to the actuating member. The ribbon and at least two tubular members may have any one or more of a number of additional characteristics including material type, coating, and integration with other components.

Another illustrative but non-limiting example may be found in a restraining mechanism for an intravascular filtering device that may include a sleeve adapted to wrap around the filter one revolution and apply a restraining force to a plurality of support struts of the filtering device. The device may also include an actuating member slidably engaged with at least two tubular members attached to the sleeve. The actuating member may be configured to release the restraining force to allow outward expansion of the plurality of support struts upon moving the actuating member in a proximal direction. The sleeve may be non-removably coupled to the actuating member. The sleeve and at least two tubular members may have any one or more of a number of additional characteristics including material type, coating, and integration with other components.

The above summary is not intended to describe each possible embodiment or every implementation of the claimed invention. The Figures, Detailed Description, and Examples which follow more particularly exemplify the embodiments described above.

DETAILED DESCRIPTION

This disclosure generally relates to embolic protection filters and restraining mechanisms that can be used to limit movement of an expandable portion of an embolic protection device. For instance, when the device is a percutaneous filter having one or more biased struts, the restraining mechanism may be configured in such a way as to substantially surround the struts and/or filter of the device and operate to prevent expansion of the struts until the physician or medical technician releases the restraining mechanism. Optionally, the restraining mechanism may prevent unwanted contact between the filtering device and the wall of the blood vessel.

Figure 1:
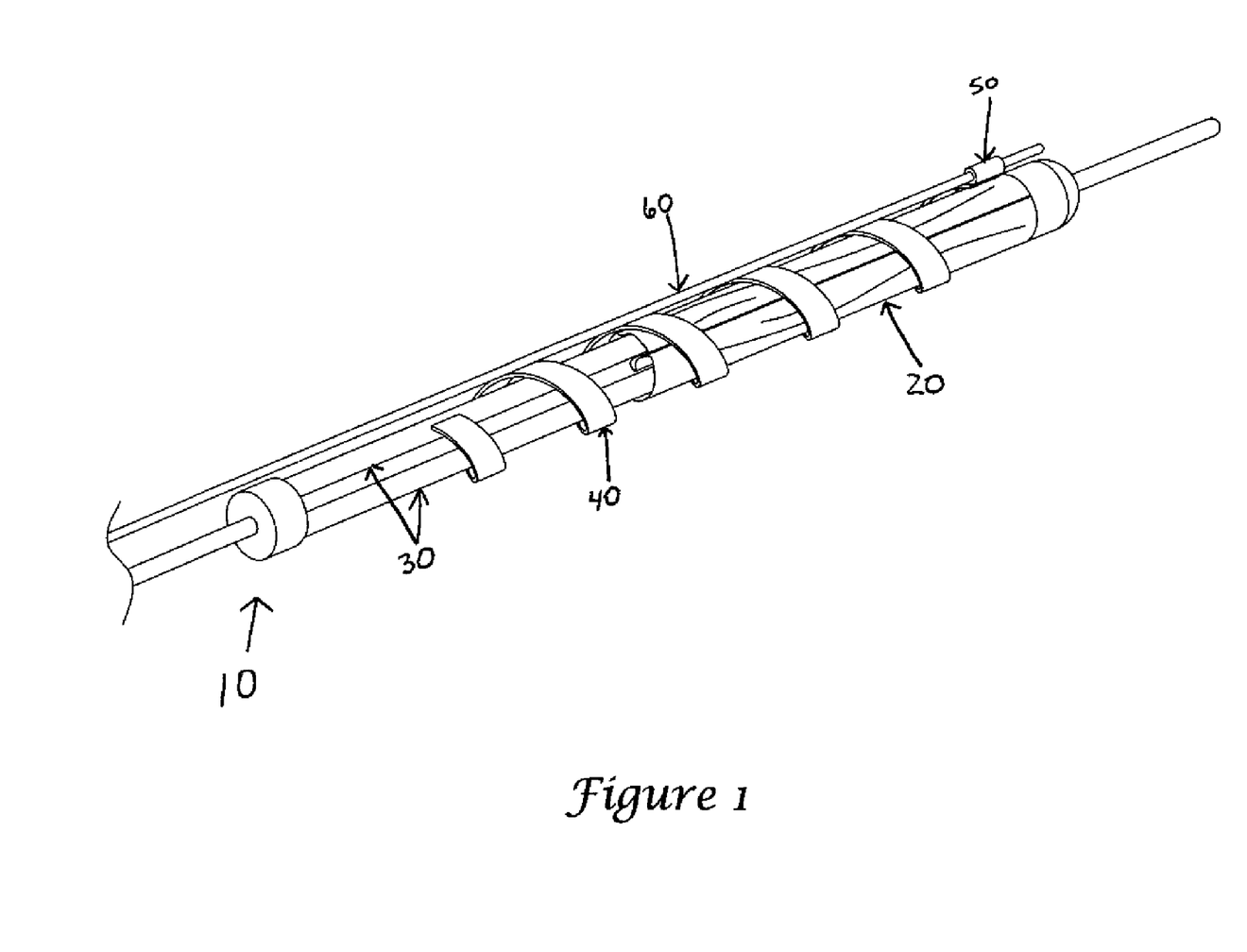
FIG. 1—illustrates a perspective view of an exemplary restraining mechanism according to one embodiment.

Referring now to FIG. 1 showing a restrained view of a medical device, illustrated is one exemplary embodiment of an intravascular filtering device 10, including filter 20 with a plurality of support struts 30 held in a closed position by ribbon 40. Ribbon 40 acts as a restraining member or mechanism that applies a force against struts 30 to prevent the struts from extending outwardly.

Ribbon 40 surrounds struts 30 and filter 20. Ribbon 40 is fixedly attached to filtering device 10 (such as to filter 20 or strut 30, for example) on one of the proximal or distal ends of the ribbon, and includes a tubular member 50 on the other end of the ribbon configured to slidably receive actuating member 60 therein. The attachment points of the ribbon 40 to the filtering device 10 and tubular member 50 may be interchanged as desired. This exemplary embodiment includes a single tubular member 50, but as will be shown in other embodiments and examples herein, additional tubular members may be used.

Ribbon 40 may wrap around struts 30 and filter 20 in a substantially helical configuration at least one full revolution. It will be appreciated that ribbon 40 may wrap around filtering device 10 multiple times—as many as is needed to restrain the device for insertion into a vessel of a patient.

Ribbon 40 may be formed from a variety of different materials, so long as the material is sufficiently strong to secure struts 30 while being flexible enough to wrap filtering device 10 without damaging any components thereof. For example, ribbon 40 can be fabricated from a metallic film, such as stainless steel or nickel-titanium alloy. Additionally, ribbon 40 may be made from various types of polymer or silicone films, such as but not limited to, heat shrink plastic, nylon, urethane, polymer, low-density polyethylene (LDPE), polyethylene terphthalate (PET), polytetrafluoroethylene (PTFE), fluorinated ethylene propylene (FEP), polyethylene (PE), polyurethane (PU), or silicone tubing.

Further, ribbon 40 may be coated with any one of, or a combination of, substances such as but not limited to, coatings to improve lubricity, reduce platelet aggression, or having anti-thrombogenic properties, hydrophilic coatings, hydrophobic coatings, heparinized coatings, anti-coagulant coatings, Teflon, silicone, medically-useful drugs, or other coatings. Ribbon 40 may also include one or more markers that are visible under fluoroscopy.

With continued reference to FIG. 1, tubular member 50 is fixedly attached to ribbon 40. Tubular member 50 may be integrally formed with ribbon 40 using the same or a different material, or it may be fastened to the ribbon using any available and commonly known means including, but not limited to, adhesives; sonic, vibration, or heat welding; or any of a variety of mechanical fastening techniques. Tubular member 50 may be formed from any suitable metal, plastic, or polymer material, and may be coated as needed or desired. Tubular member 50 may include a radiopaque material.

Material selection of the various components of the restraining mechanism, such as radiopaque materials and/or markers visible under fluoroscopy, can help the physician determine if the device has properly deployed once it has been inserted into the vessel of a patient.

Tubular member 50 is configured to slidably receive actuating member 60 therein. Actuating member 60 may take the form of a wire, rod, or fiber, in any suitable shape or configuration. Actuating member 60 may be formed from any appropriate material, including but not limited to, metals or alloys such as nickel-titanium alloy or stainless steel; any suitable nylon, polyethylene, or any other appropriate polymer or plastic; composites; synthetic materials; or any combination thereof. Actuating member 60 may also include a lubricious or any other appropriate coating.

Figure 2:
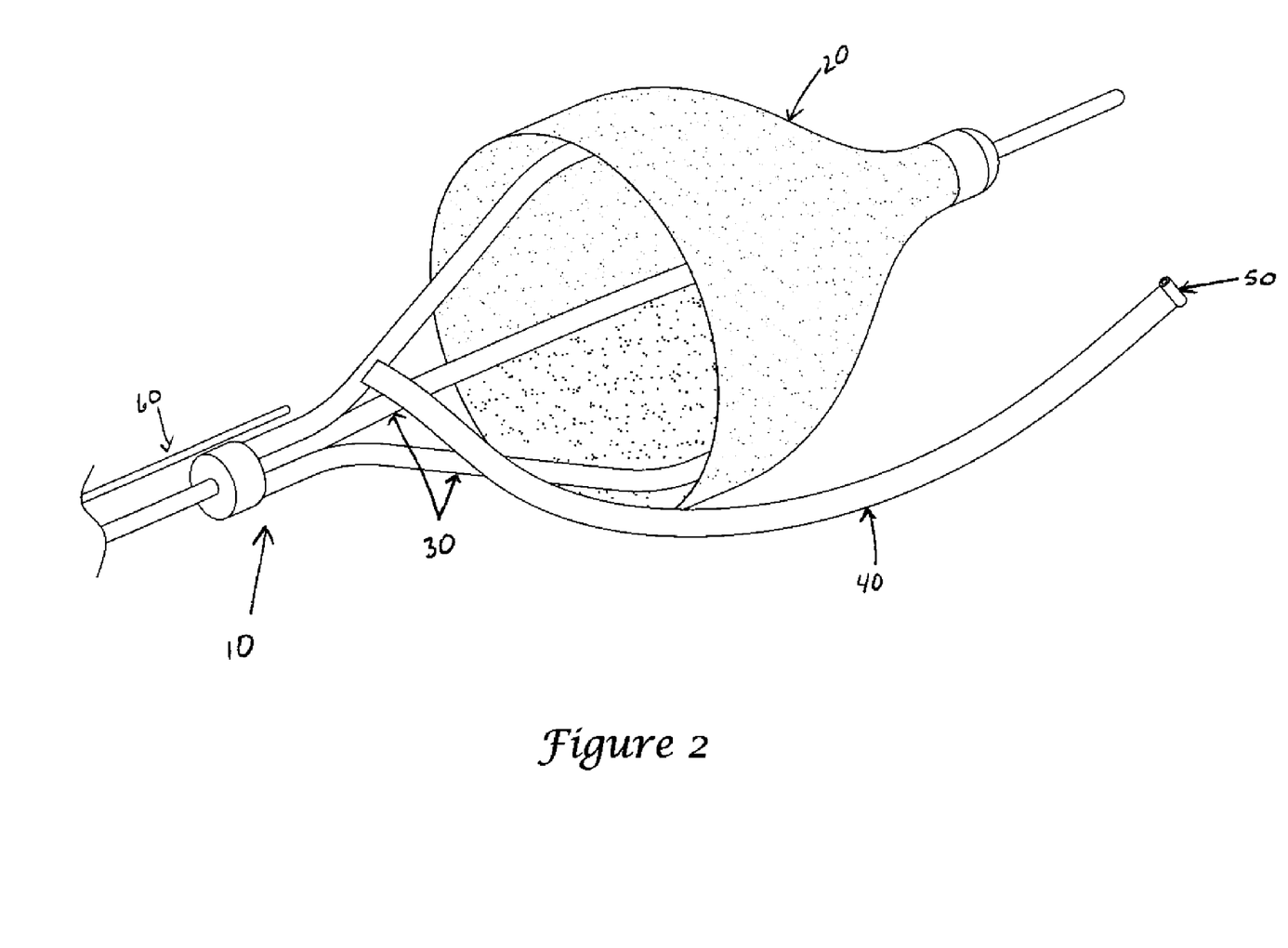
FIG. 2—illustrates a perspective view of the exemplary restraining mechanism of FIG. 1 showing an actuating member moved in a proximal direction.

FIG. 2 shows filtering device 10 of FIG. 1 in a deployed configuration. In this configuration, filtering device 10 can include a plurality of support struts 30 that are biased to extend outwardly. Support struts 30 may be at least partially constructed of a shape memory material, including but not limited to, shape memory metals such as NiTiNOL; shape memory polymers such as polyurethane; polycycloocetene; cross-linked polyethylene; thermoplastics such as shape memory polyurethanes, polyethylene, polynorborene polymers and copolymers and blends thereof with styrene elastomer copolymers, such as Kraton, and cross-linked transpolyoctylene rubber; cross-linked polyisoprene; styrene butadiene copolymers; bioabsorbable shape memory polymers such as polycaprolactone, copolymers, and/or PLLA PGA copolymers; PMMA; Azodyes, Zwitterionic and other photo chromatic materials.

In continuing reference to FIG. 2, actuating member 60 has been moved proximal to disengage the actuating member from tubular member 50. This serves to release the restraining force applied to the plurality of support struts 30 by ribbon 40, allowing the biased support struts to expand outward and deploy filter 20. In this example, filter 20 is attached to at least one of support struts 30 and is configured to capture material of a variety of sizes and enable removal of the captured material. Filter 20 has a variety of pores or holes through which fluid can pass, while the size and/or shape of each pore or hole is selected to prevent passage of emboli or other material.

Filter 20 can comprise a microporous membrane formed from a polymeric material. Examples of suitable polymeric materials include polypropylene (PP), polyvinylchloride (PVC), polyamide (nylon), polyurethane, polyester, polyethylene tetraphlalate, polyether-ether ketone (PEEK), polyether block amide (PEBA), polytetraflouroethylene (PTFE), or any mixture, blend or combination thereof. Alternatively, the filter membranes can comprise a woven, braided, or otherwise manufactured mesh screen made from a metallic material such as stainless steel or nickel-titanium alloy.

Figure 3:
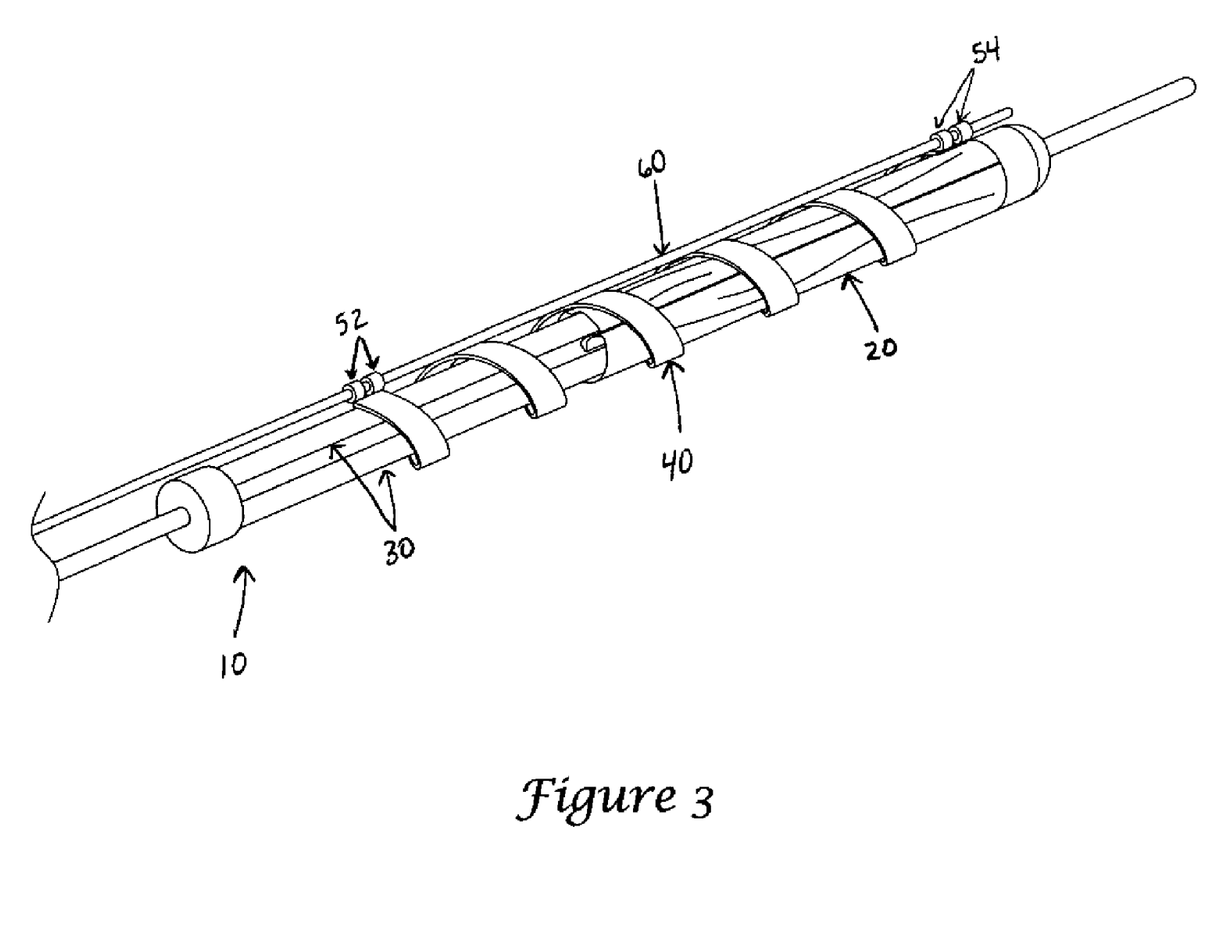
FIG. 3—illustrates a perspective view of an exemplary restraining mechanism according to one embodiment.

Another exemplary embodiment includes a filtering device 10 with support struts 30, filter 20, and ribbon 40. However, as shown in FIG. 3, this embodiment detaches ribbon 40 from filtering device 10 and adds additional tubular members 52, 54, when compared to the embodiment of FIG. 1. Ribbon 40 may wrap around struts 30 and filter 20 in a substantially helical configuration at least one full revolution. It will be appreciated that ribbon 40 may wrap around filtering device 10 multiple times—as many as is needed to restrain the device for insertion into a vessel of a patient. Tubular members 52, 54 are engaged by actuating member 60. As with the embodiment discussed above (with respect to FIG. 1), tubular members 52, 54 are fixedly attached to ribbon 40. Tubular members 52, 54 may be integrally formed with ribbon 40 using the same or a different material, or may be fastened to the ribbon as discussed above. Tubular members 52, 54 may be formed from any suitable metal, plastic, or polymer material, and may be coated as needed or desired. Tubular members 52, 54 may include a radiopaque material.

Material selection of the various components of the restraining mechanism, such as radiopaque materials and/or markers visible under fluoroscopy, can help the physician determine if the device has properly deployed once it has been inserted into the vessel of a patient.

Tubular members 52, 54 are configured to slidably receive actuating member 60 therein. Actuating member 60 may take the form of a wire, rod, or fiber, in any suitable shape or configuration. Actuating member 60 may be formed from any appropriate material as discussed above. Actuating member 60 may also include a lubricious or any other appropriate coating.

Tubular members 52, 54 are preferred, but not required, to be oriented in a coaxial fashion when ribbon 40 is restraining filtering device 10. Coaxial orientation improves performance when moving actuating member 60 within tubular members 52, 54 by reducing the amount of force required to move the actuating member. However, other orientations of tubular members 52, 54 and actuating member 60 may provide acceptable performance, such as but not limited to, having the center bore of the tubular members 52, 54 substantially parallel to one another and having an offset (not shown) in actuating member 60.

Figure 3A:
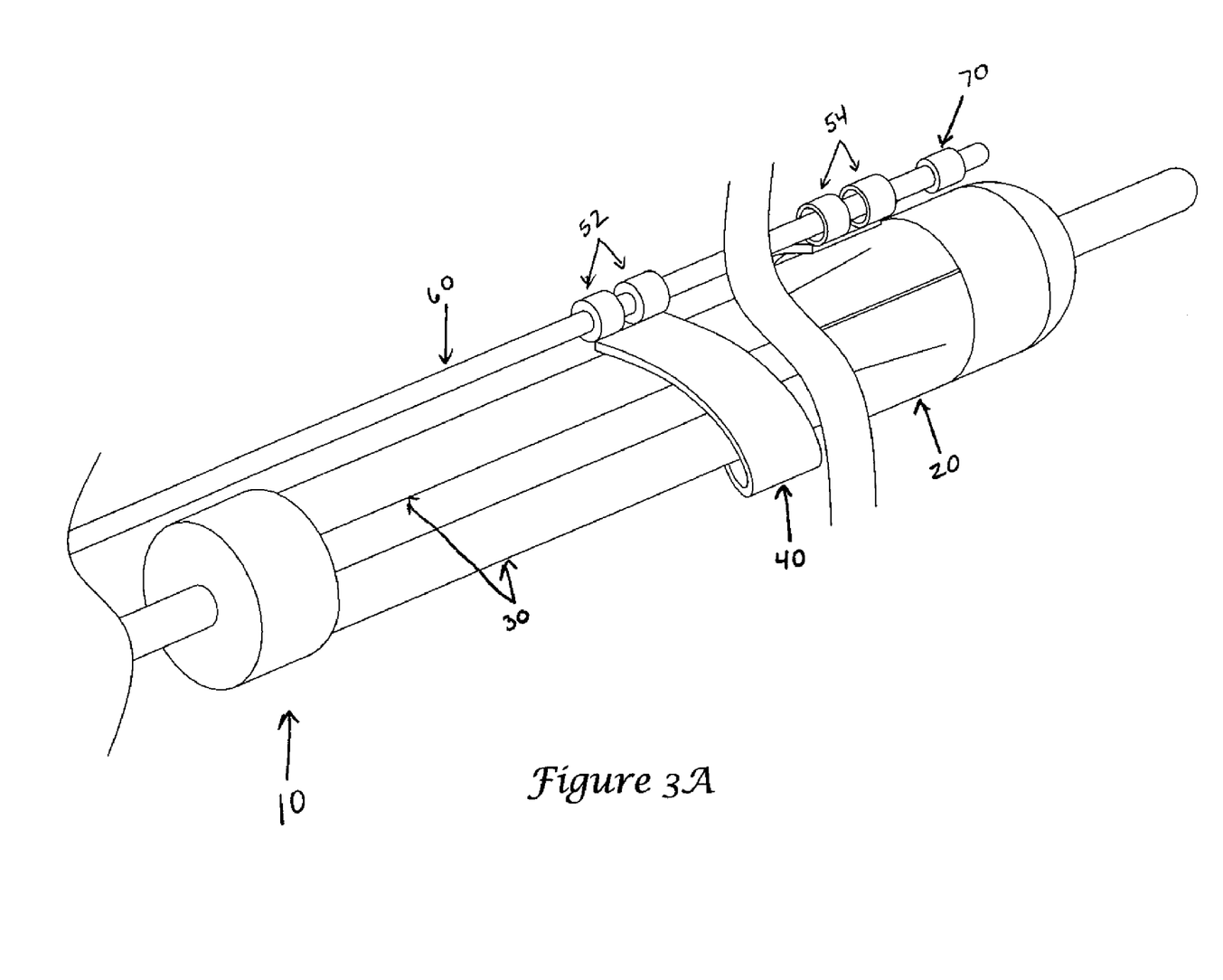
FIG. 3A—illustrates a detailed view of a portion of the restraining mechanism of FIG. 3 according to one exemplary embodiment.
Figure 3B:
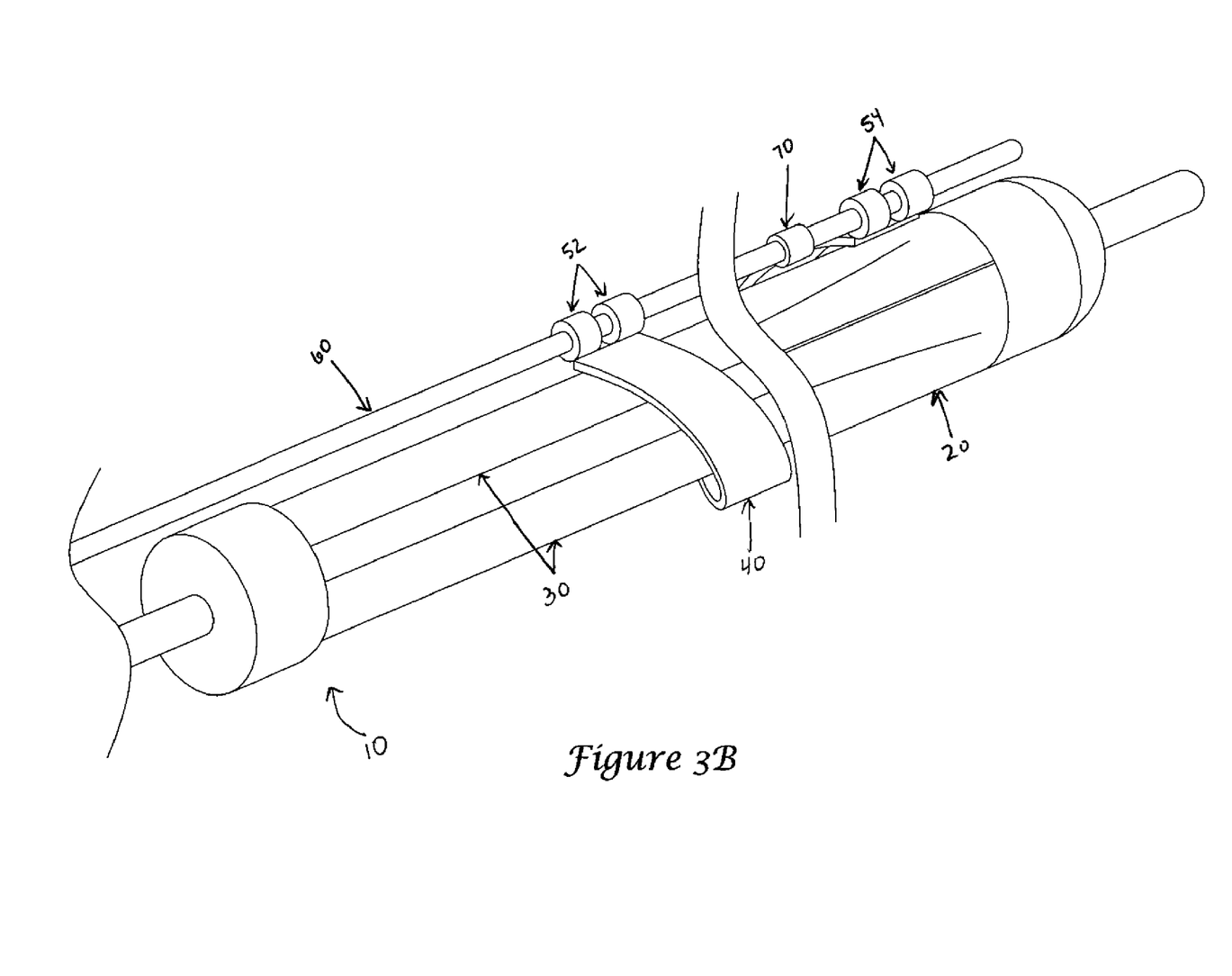
FIG. 3B—illustrates a detailed view of a portion of the restraining mechanism of FIG. 3 according to one exemplary embodiment.

The embodiment shown in FIG. 3 depicts tubular members 52, 54 on each of the proximal and distal ends of ribbon 40. In order to avoid leaving ribbon 40 free within the vessel of the patient, tubular members 52, 54 and actuating member 60 are configured so as to retain at least a portion of the ribbon coupled to the actuating member following release of the restraining force. This can be accomplished in a variety of ways, one of which has already been described—using an offset on actuating member 60 such that at least one of the tubular members 52, 54 cannot be disengaged from the actuating member. FIGS. 3A and 3B illustrate exemplary means of configuring actuating member 60 and tubular members 52, 54 of FIG. 3.

FIG. 3A depicts a distal stopping feature 70 on actuating member 60. Distal stopping feature 70 and tubular members 54 are configured such that the distal stopping feature may pass through one or more tubular members, but may not pass through at least one tubular member 52. For example, distal stopping feature 70 may have a diameter larger than actuating member 60, but a smaller diameter than the inside of the distalmost tubular member 54, and a larger diameter than the inside of the proximalmost tubular member 52.

FIG. 3B depicts a stopping feature 70 on actuating member 60 located between tubular members 52, 54. Placement of stopping feature 70 in this approximate location allows actuating member 60 to disengage tubular members 54 that are distal the stopping feature while retaining engagement with the tubular member or members 52 proximal the stopping feature. An additional benefit of this arrangement is that less movement of actuating member 60 is required to disengage tubular members 54. In the event that an offset in actuating member 60 were used, placement of the offset could be similar to that of stopping feature 70. Another example stopping feature (not shown) may include a retractable and/or spring-loaded stopping feature that may pass through a tubular member in the distal direction, but cannot be pulled back through in the proximal direction.

Figure 4:
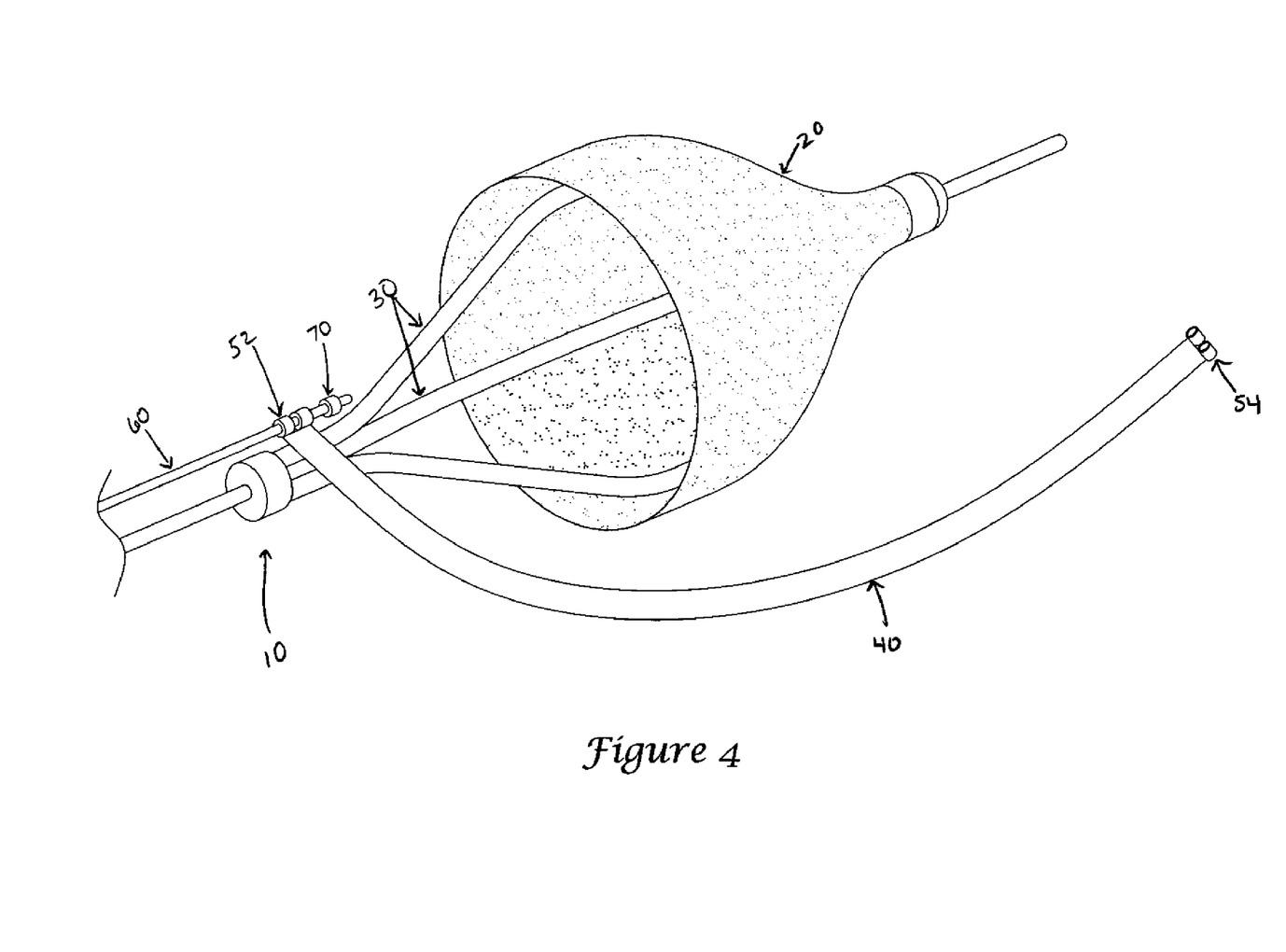
FIG. 4—illustrates a perspective view of the exemplary restraining mechanism of FIG. 3 showing an actuating member moved in a proximal direction.

FIG. 4 illustrates exemplary filtering device 10 of FIG. 3 in a deployed configuration. Actuating member 60 is disengaged from at least one tubular member 54, allowing ribbon 40 to unfurl and support struts 30 to expand and deploy filter 20. Ribbon 40 remains at least partially coupled to actuating member 60 via at least one tubular member 52 that is still engaged by actuating member 60.

Figure 5:
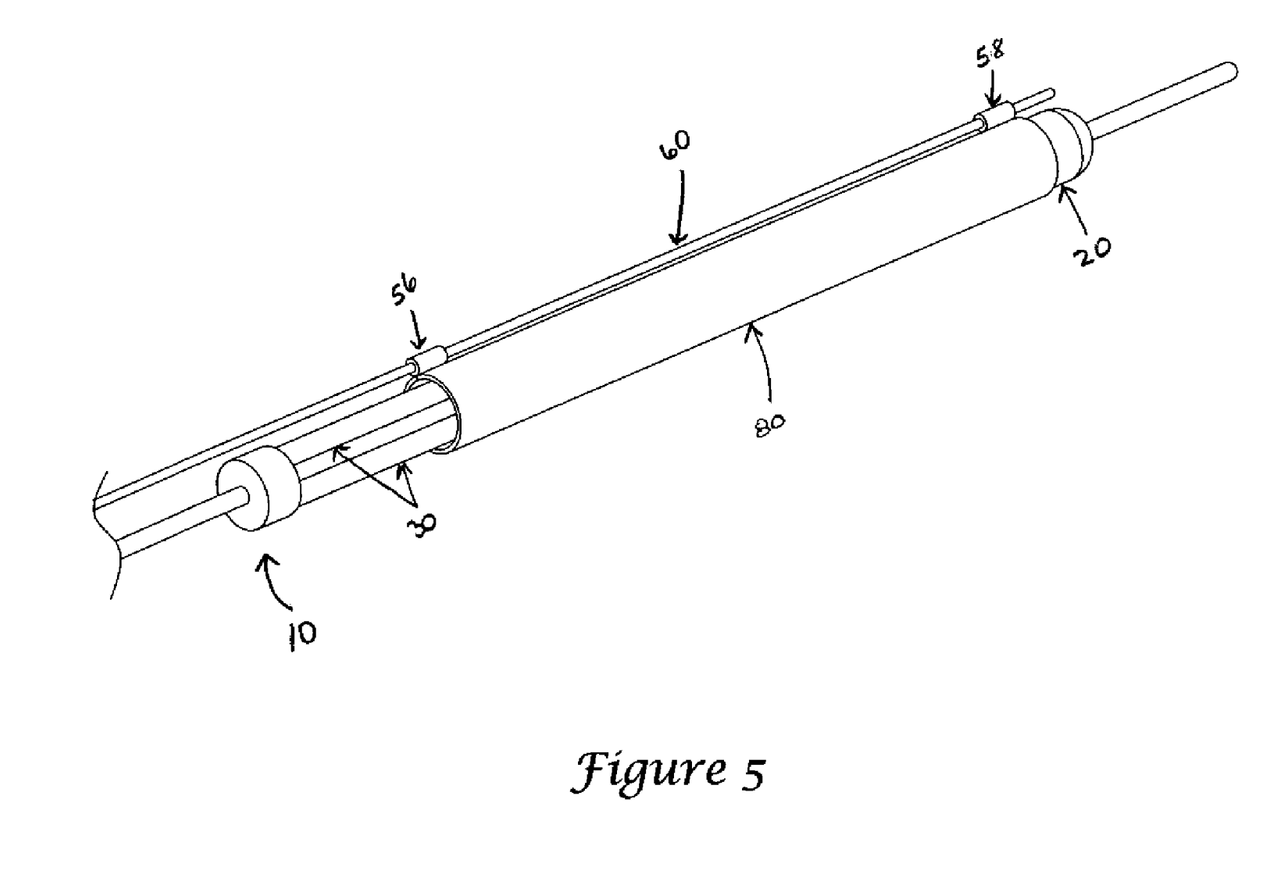
FIG. 5—illustrates a perspective view of an exemplary restraining mechanism according to one embodiment.

Another exemplary embodiment is illustrated by FIG. 5. FIG. 5 in configured similar to the embodiment of FIG. 3 above, except that ribbon 40 has been replaced by sleeve 80. Sleeve 80 may wrap around support struts 30 and filter 20 one full revolution, with at least two tubular members 56, 58 being engaged by actuating member 60 to provide a restraining force to maintain the support struts and filter in a collapsed position.

Tubular members 56, 58 are fixedly attached to sleeve 80. Tubular members 56, 58 may be integrally formed with sleeve 80 using the same or a different material, or may be fastened to the sleeve as discussed above. Tubular members 56, 58 may be formed from any suitable metal, plastic, or polymer material, and may be coated as needed or desired. Tubular members 56, 58 may include a radiopaque material.

Material selection of the various components of the restraining mechanism, such as radiopaque materials and/or markers visible under fluoroscopy, can help the physician determine if the device has properly deployed once it has been inserted into the vessel of a patient.

Tubular members 56, 58 are configured to slidably receive actuating member 60 therein. Actuating member 60 may take the form of a wire, rod, or fiber, in any suitable shape or configuration. Actuating member 60 may be formed from any appropriate material as discussed above. Actuating member 60 may also include a lubricious or any other appropriate coating.

Tubular members 56, 58 are preferred, but not required, to be oriented in a coaxial fashion when sleeve 80 is restraining filtering device 10. Coaxial orientation improves performance when moving actuating member 60 within tubular members 56, 58 by reducing the amount of force required to move the actuating member. However, other orientations of tubular members 56, 58 and actuating member 60 may provide acceptable performance, such as but not limited to, having the center bore of the tubular members substantially parallel to one another and having an offset (not shown) in actuating member 60.

Figure 5A:
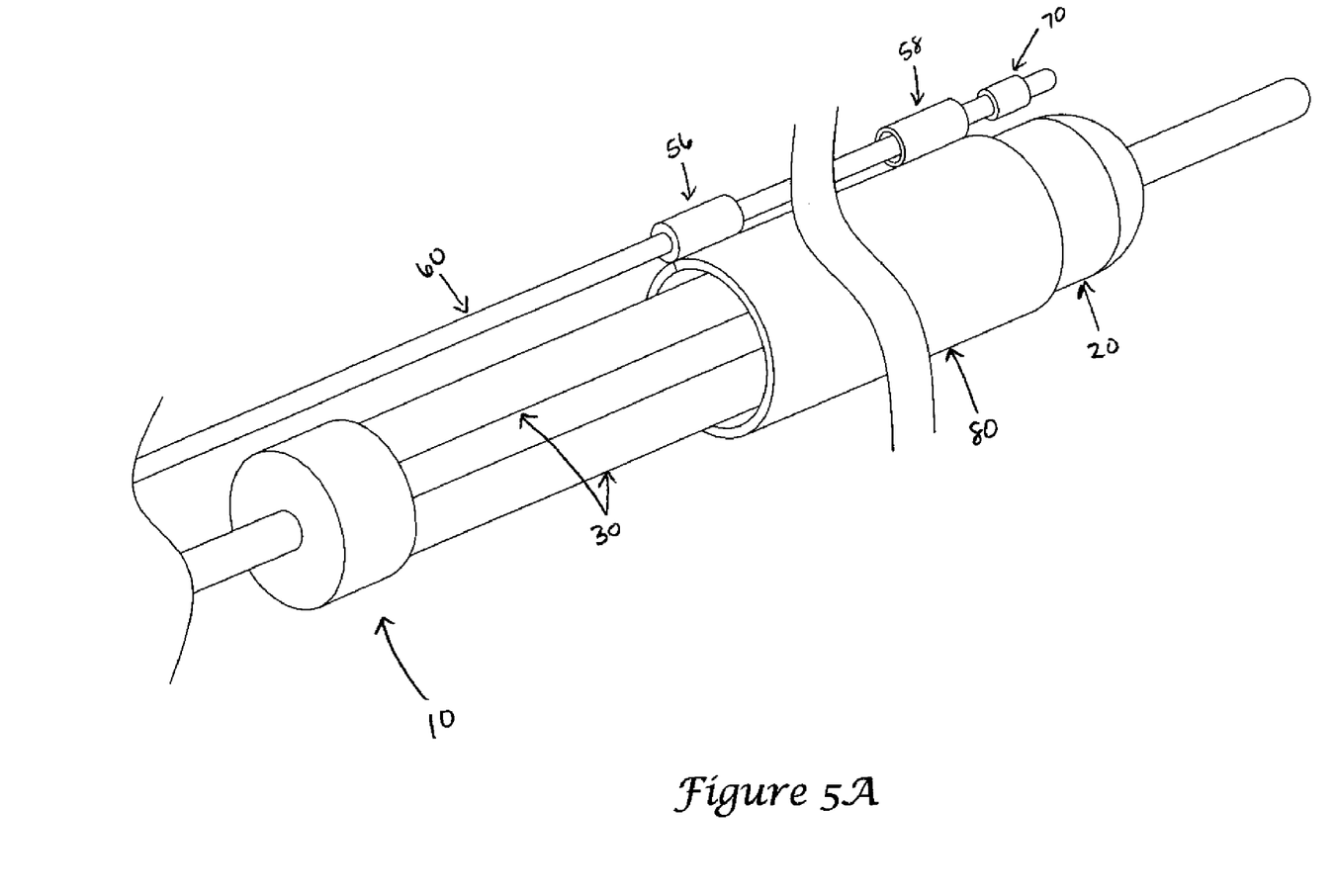
FIG. 5A—illustrates a detailed view of a portion of the restraining mechanism of FIG. 5 according to one exemplary embodiment.
Figure 5B:
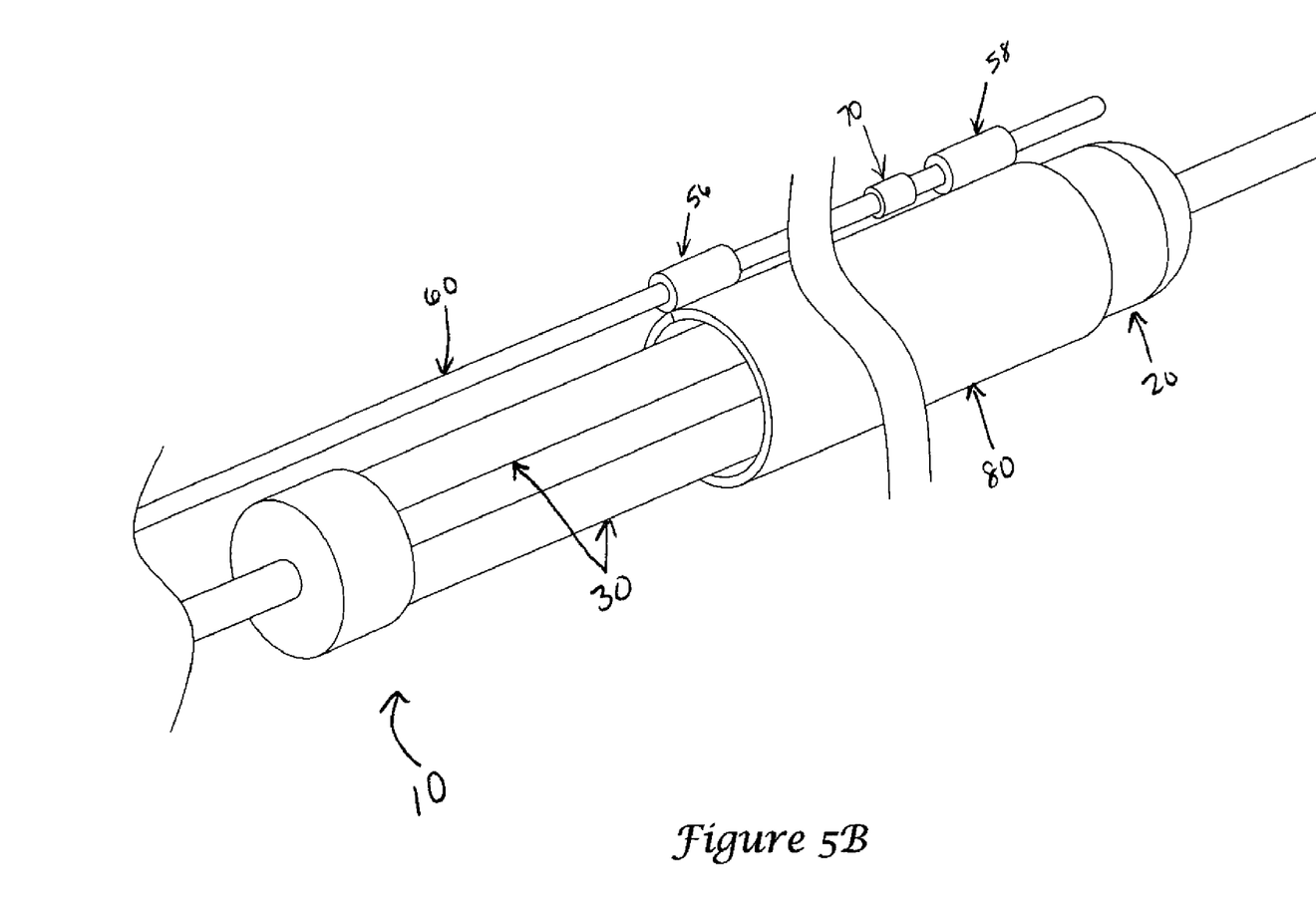
FIG. 5B—illustrates a detailed view of a portion of the restraining mechanism of FIG. 5 according to one exemplary embodiment.

The exemplary embodiment shown in FIG. 5 depicts tubular members 56, 58 on each of the left and right edges of sleeve 80. In order to avoid leaving sleeve 80 free within the vessel of the patient, tubular members 56, 58 and actuating member 60 are configured so as to retain at least a portion of the sleeve coupled to the actuating member following release of the restraining force. This can be accomplished in a variety of ways, one of which has already been described—using an offset on actuating member 60 such that at least one of the tubular members 56, 58 cannot be disengaged from the actuating member. FIGS. 5A and 5B illustrate exemplary means of configuring actuating member 60 and tubular members 56, 58 of FIG. 5.

FIG. 5A depicts a distal stopping feature 70 on actuating member 60. Distal stopping feature 70 and tubular members 56, 58 are configured such that the distal stopping feature may pass through one or more tubular members 58, but may not pass through at least one tubular member 56. For example, distal stopping feature 70 may have a diameter larger than actuating member 60, but a smaller diameter than the inside of the distalmost tubular member 58, and a larger diameter than the inside of the proximalmost tubular member 56. As in the examples illustrated in FIGS. 3, 3A, 3B, and 4, the number of tubular members 56, 58 may vary, and multiple tubular members may be used in any particular area.

FIG. 5B depicts a stopping feature 70 on actuating member 60 located between tubular members 56, 58. Placement of stopping feature 70 in this approximate location allows actuating member 60 to disengage tubular members 58 that are distal the stopping feature while retaining engagement with the tubular member or members 56 proximal the stopping feature. An additional benefit of this arrangement is that less movement of actuating member 60 is required to disengage tubular members 58. In the event that an offset in actuating member 60 were used, placement of the offset could be similar to that of stopping feature 70. Another example stopping feature (not shown) may include a retractable and/or spring-loaded stopping feature that may pass through a tubular member in the distal direction, but cannot be pulled back through in the proximal direction.

Those skilled in the art will recognize that the invention may be manifested in a variety of forms other than the specific embodiments described and contemplated herein. For example, at least some of the electronic messages transmitted and received during the operation of the last payment module may be replaced by an alternate means of communication such as paper mail or telephonic communication among individuals without departing from the spirit of the invention. Accordingly, departure in form and detail may be made without departing from the scope and spirit of the invention as described in the appended claims.

The invention claimed is:

1. A restraining mechanism configured to prevent outward expansion of a plurality of support struts, the restraining mechanism comprising:
   an intravascular filtering device including the plurality of support struts and a filter attached to at least one of the plurality of struts;
   a ribbon having a proximal end, a distal end, and at least two tubular members configured to receive an actuating member; and
   an actuating member configured to slidably engage the at least two tubular members, the actuating member including a distal stopping feature configured such that the distal stopping feature cannot pass through at least one of the two tubular members;
   wherein the ribbon is adapted to wrap around the filtering device at least one revolution and applies a restraining force to the plurality of support struts to prevent the plurality of support struts from expanding outward;
   wherein the actuating member is configured to release the restraining force of the ribbon and allow the outward expansion of the plurality of support struts when the actuating member is moved in a proximal direction; and
   wherein the ribbon is non-removably coupled to the actuating member;
   wherein the ribbon has at least one tubular of the two members fixedly attached to each of the proximal end and the distal end of the ribbon.

2. The restraining mechanism of claim 1, wherein the ribbon is adapted to wrap around the filter in a substantially helical configuration.

3. The restraining mechanism of claim 1, wherein the ribbon is formed of a polymer.

4. The restraining mechanism of claim 1, wherein the ribbon is formed of metal.

5. The restraining mechanism of claim 1, wherein the ribbon is coated with or comprised of anti-coagulant, hydrophobic, or hydrophilic coatings.

6. The restraining mechanism of claim 1, wherein the ribbon is drug-coated.

7. The restraining mechanism of claim 1, wherein the ribbon includes one or more markers visible under fluoroscopy.

* * * * *

UNITED STATES PATENT AND TRADEMARK OFFICE
CERTIFICATE OF CORRECTION

PATENT NO.        : 8,388,645 B2
APPLICATION NO.   : 12/643029
DATED             : March 5, 2013
INVENTOR(S)       : Grace Tripp, Michele Zoromski and Jim Anderson It is certified that error appears in the above-identified patent and that said Letters Patent is hereby corrected as shown below:

In the Claims:

Column 8, Claim 1,
Line 11: Delete "one tubular of the two members" and insert -- one of the two tubular members --.

Signed and Sealed this
Ninth Day of July, 2013

Teresa Stanek Rea
*Acting Director of the United States Patent and Trademark Office*